United States Patent [19]

Kabbe et al.

[11] 4,185,112
[45] Jan. 22, 1980

[54] COMBATING ARTHROPODS WITH 2-SUBSTITUTED-CHROMAN-4-ONES

[75] Inventors: Hans-Joachim Kabbe, Leverkusen; Peter Roessler, Berg.Gladbach, both of Fed. Rep. of Germany

[73] Assignee: Bayer Aktiengesellschaft, Leverkusen, Fed. Rep. of Germany

[21] Appl. No.: 947,285

[22] Filed: Sep. 29, 1978

[30] Foreign Application Priority Data

Oct. 7, 1977 [DE] Fed. Rep. of Germany ....... 2745306

[51] Int. Cl.² .............................................. A01N 9/28
[52] U.S. Cl. ................................... 424/283; 424/267; 424/274
[58] Field of Search ..................... 424/283, 267, 274

[56] References Cited

U.S. PATENT DOCUMENTS 4,065,574   12/1977   Moon et al. ..................... 424/283

OTHER PUBLICATIONS

Bowers et al., "Science", vol. 193 (1976), pp. 542–547.
Chemical Abstracts, vol. 79 (1973), p. 91908x.
Chemical Abstracts, vol. 69 (1968), p. 106557b.

*Primary Examiner*—V. D. Turner

*Attorney, Agent, or Firm*—Sprung, Felfe, Horn, Lynch & Kramer

[57] ABSTRACT

Known 2-substituted-chroman-4-ones of the formula

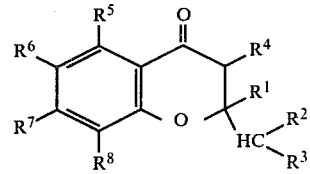

wherein
R¹ to R⁴ each independently is hydrogen, various hydrocarbyl groups, alkoxycarbonyl, carboxyl or aminoalkyl, or
R² can also be an amino radical, or
R¹ and R² can complete a carbocyclic or heterocyclic ring, and
R⁵ to R⁸ each independently is hydrogen, halogen hydroxyl, nitro, cyano, carboxyl, various hydrocarbyl or hydrocarbyloxy groups, alkoxycarbonyl, alkylamino or acylamino are effective in combating arthropods, being applied to the arthropods or their habitat such as soil, plants and domesticated animals.

2 Claims, No Drawings

COMBATING ARTHROPODS WITH 2-SUBSTITUTED-CHROMAN-4-ONES

The present invention relates to the use as arthropodicides (especially as insecticides and acaricides) of certain chroman-4-ones, which are known.

It has already been disclosed that chromanones possess herbicidal and antioxidative properties (see United States Application Ser. No. 853,932, filed Nov. 22, 1977, now pending).

Further, it has been disclosed that certain chromenes, for example Precocene I and Precocene II, exhibit development-inhibiting properties (Chem. Eng. News 1976, No. 16, page 19). Their action is however not entirely satisfactory, above all if low amounts are used.

It has been found that the known chroman-4-ones of the general formula

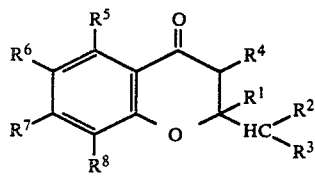

(I)

wherein
$R^1$ to $R^4$, which need not be identical, each represent hydrogen, an optionally substituted alkyl, alkenyl, cycloalkyl, aryl, aralkyl or alkoxycarbonyl group, carboxyl or aminoalkyl,
$R^2$ can alternatively represent amino or optionally substituted dialkylamino, or
$R^1$ and $R^2$ can, conjointly with the adjoining carbon atoms, form a carbocyclic or heterocyclic ring, and
$R^5$ to $R^8$, which need not be identical, each represent hydrogen, halogen, hydroxyl, nitro, cyano, carboxyl, an optionally substituted alkyl, alkenyl, cycloalkyl, aryl, aralkyl, alkoxy, aralkoxy, aryloxy, alkoxycarbonyl, alkylamino or dialkylamino group, amino or acylamino,
exhibit arthropodicidal, and in particular powerful insecticidal and acaricidal, properties.

Accordingly, the present invention provides an arthropodicidal composition containing as active ingredient a compound of the formula (I), in admixture with a solid or liquefied gaseous diluent or carrier or in admixture with a liquid diluent or carrier containing a surface-active agent.

The present invention also provides a method of combating arthropods, especially insects or acarids, which comprises applying to the arthropods, or to a habitat thereof, a compound of the formula (I) alone or in the form of a composition containing as active ingredient a compound of the formula (I) in admixture with a diluent or carrier.

Surprisingly, the active compounds according to the invention exhibit a substantially better action than the compounds of similar structure and of analogous action, known from the prior art. The new use of the active compounds thus represents an enrichment of the art.

In general formula (I), optionally substituted alkyl or alkenyl radicals ($R^1$ to $R^8$) which may be mentioned are straight-chain or branched alkyl or alkenyl radicals with up to 18, preferably up to 12, and especially up to 6, carbon atoms. As examples of these there may be mentioned: methyl, ethyl, propyl, isopropyl, butyl, isobutyl, tert.-butyl, hexyl, nonyl, decyl, undecyl, octadecyl, but-3-enyl, 4-methyl-pent-3-enyl and 4,8-dimethylnona-3,7-dienyl.

Examples of suitable optionally substituted cycloalkyl radicals ($R^1$ to $R^8$) are those with 3 to 18, preferably with 4 to 12, and especially with 5 or 6, carbon atoms, for example cyclopropyl, cyclobutyl, cycloheptyl, cyclooctyl, cyclododecyl, cycloheptadecyl and cyclooctadecyl, and, preferably, cyclopentyl or cyclohexyl.

Optionally substituted aryl radicals ($R^1$ to $R^8$) which may be mentioned are those with 6 to 14 carbon atoms, such as naphthyl, and, preferably, phenyl.

Examples of suitable optionally substituted aralkyl radicals ($R^1$ to $R^8$) are those with 7 to 18 carbon atoms wherein the aliphatic part contains 1 to 8, preferably 1 to 4, carbon atoms and the aromatic part is a carbocyclic radical with 6 to 10 carbon atoms. The following aralkyl radicals may be mentioned as examples: phenylethyl, phenylpropyl, phenylbutyl, naphthylmethyl and naphthylethyl and, preferably, benzyl.

When $R^1$ is linked to $R^2$ to form an optionally substituted ring, this ring may be either carbocyclic or heterocyclic.

Examples of suitable carbocyclic rings ($R^1/R^2$) are rings containing saturated or unsaturated hydrocarbon members, preferably 3-membered to 12-membered rings. It is also possible for the carbocyclic rings to be fused to one or more radicals from the benzene series.

As examples of carbocyclic radicals there may be mentioned: cyclopropane, cyclopentane, cyclohexane, cycloheptane, cyclooctane, cyclononane, cyclodecane, cycloundecane, cyclododecane, cyclohexene, cyclooctene, cyclododecene and tetralin.

Examples of suitable heterocyclic rings ($R^1/R^2$) are 5-membered to 12-membered rings, preferably 5-membered and 6-membered rings, which in addition to hydrocarbon members also contain one or more heteroatoms, for example nitrogen, oxygen or sulphur. The heterocyclic rings can contain 1 or 2 double bonds and can furthermore be fused to one or more radicals from the benzene series. As examples of heterocyclic radicals there may be mentioned piperidine, pyrrolidine, tetrahydrofuran, tetrahydropyrane and tetrahydrothiopyrane.

In respect of their number of carbon atoms, the alkyl and aryl radicals of the alkoxy, alkoxycarbonyl, alkylamino, dialkylamino, aryloxy and aralkoxy radicals correspond to the range of meanings given above.

As preferred alkoxy groups there may be mentioned those with up to 4 carbon atoms, such as methoxy, ethoxy, propoxy, isopropoxy, butoxy, isobutoxy and tert.-butoxy.

As preferred aryloxy groups there may be mentioned those with 6 to 10 carbon atoms, such as phenoxy or naphthoxy.

As preferred aralkoxy groups there may be mentioned those with 7 to 10 carbon atoms, such as benzyloxy, phenylethoxy, phenylpropoxy, phenylisopropoxy, phenylbutoxy, phenylisobutoxy and phenyl tert.-butoxy.

As preferred alkoxycarbonyl groups there may be mentioned those with up to 4 carbon atoms the alkyl radical, such as methoxycarbonyl, ethoxycarbonyl, propoxycarbonyl and isopropoxycarbonyl.

As preferred alkylamino and dialkylamino groups there may be mentioned those with up to 3 carbon atoms per alkyl radical, such as methylamino, ethylamino, isopropylamino, dimethylamino, diethylamino, dipropylamino and diisopropylamino. It is also possible for the two alkyl radicals of the dialkylamino group to be joined to form a ring, for example pyrrolidinyl or piperidinyl.

The acylamino group ($R^5$ to $R^8$) can be an aliphatic or aromatic radical, in which case the aliphatic and the aromatic radical conform to the above-mentioned range of meanings. As examples of acylamino groups there may be mentioned formylamino, acetylamino, propionylamino, valeroylamino and benzoylamino.

As halogens there may be mentioned fluorine, chlorine, bromine and iodine, preferably chlorine.

Suitable substituents of the alkyl, alkenyl, cycloalkyl, aryl, aralkyl, alkoxy, aralkoxy, aryloxy, alkoxycarbonyl, alkylamino and dialkylamino groups of the radicals $R^1$ to $R^8$ are substituents which do not undergo change under the reaction conditions. Examples which may be mentioned are halogens, namely fluorine, chlorine, bromine and iodine, cyano, $C_1$-$C_6$-alkyl, $C_1$-$C_6$-alkoxy, ($C_1$-$C_6$-alkoxy)-carbonyl, ($C_1$-$C_6$-alkoxy)carbonyl($C_1$-$C_6$-alkyl), amino, $C_1$-$C_6$-alkylamino, di-($C_1$-$C_6$-alkyl)amino, an aryl radical from the benzene series, or a carboxylic acid group.

The following may be mentioned as examples of the chroman-4-ones of the formula (I) which can be used according to the invention: 2,2-pentamethylenechroman-4-one, 2,2-pentamethylene-7-hydroxychroman-4-one, 2,2-pentamethylene-6-hydroxychroman-4-one, 2,2-pentamethylene-6-methoxychroman-4-one, 2,2-pentamethylene-7-methoxychroman-4-one, 7-acetylamino-2,2-pentamethylenechroman-4-one, 6-cyclohexyl-2,2-pentamethylenechroman-4-one, 5-chloro-7-phenyl-2,2-pentamethylenechroman-4-one, 7-alkyloxy-2,2-pentamethylenechroman-4-one, 6-ethoxycarbonylmethoxy-2,2-pentamethylenechroman-4-one, 6-nitro-2,2-pentamethylenechroman-4-one, 5-cyano-2,2-pentamethylenechroman-4-one, 7-trifluoromethyl-2,2-pentamethylenechroman-4-one, 6-carboxy-2,2-pentamethylenechroman-4-one, 7-methoxycarbonyl-2,2-pentamethylenechroman-4-one, 6-butyramido-2,2-pentamethylenechroman-4-one, 7-amino-2,2-pentamethylenechroman-4-one, 5-hydroxy-7-pentyl-2,2-pentamethylenechroman-4-one, 2-methyl-2-($\gamma$-diethylaminopropyl)-chroman-4-one, 2-methyl-2($\beta$-carboxyethyl)-chroman-4-one, 2-methyl-2-nonyl-7-hydroxychroman-4-one, 2-methyl-2-($\beta$-N-pyrrolidinylethyl)-chroman-4-one, 2-methyl-2-($\delta$-carboxybutyl)-chroman-4-one, 2,2-tetramethylenechroman-4-one, 7-hydroxy-2,2-tetramethylenechroman-4-one, 6-hydroxy-2,2-tetramethylenechroman-4-one, 8-methoxy-2,2-tetramethylenechroman-4-one, 6-ethoxy-2,2-tetramethylenechroman-4-one, 7-chloro-2,2-tetramethylenechroman-4-one, 5-bromo-2,2-tetramethylenechroman-4-one, 2-isopropyl-3-phenyl-6-methylchroman-4-one, 2,3,6-trimethyl-chroman-4-one, 5,7-dihydroxy-2,2-tetramethylenechroman-4-one, 6,8-dihydroxy-2,2-tetramethylenechroman-4-one, 5,8-dihydroxy-2,2-tetramethylenechroman-4-one, 5,7,8-trihydroxy-2,2-tetramethylenechroman-4-one, 7-benzyloxy-2,2-tetramethylenechroman-4-one, 6-dimethylamino-2-isopropyl-chroman-4-one, 7-acetamino-2-isopropylchroman-4-one, 7-chloro-2-propyl-chroman-4-one, 6-hexylamino-2-methyl-2-nonyl-chroman-4-one, 5-hydroxy-7-pentyl-2,2-tetramethylene-chroman-4one, 5-hydroxy-7-pentyl-2,2-undecamethylene-chroman-4-one, 5-hydroxy-7-heptyl-2-methyl-2-nonyl-chroman-4-one, 5-methyl-7-hydroxy-2-methyl-2-$\delta$-carboxybutyl-chroman-4-one, 6-hydroxy-2-methyl-2-$\delta$-carboxybutyl-chroman-4-one, 7-hydroxy-2-$\delta$-carboxybutyl-chroman-4-one, 5-hydroxy-7-pentyl-2-methyl-2-$\beta$-carboxyethyl-chroman-4-one, 6-hydroxy-2-methyl-2-$\beta$,$\beta$, $\beta$-trifluoroethyl-chroman-4-one, 7-hydroxy-2-methyl-2-diethylaminopropyl-chroman-4-one, 2-methyl-2-N-pyrrolidinylpropyl-chroman-4-one, 2-methyl-2-benzyl-chroman-4-one and 2-hydroxybutyl-chroman-4- one.

The active compounds are well tolerated by plants, have a favourable level of toxicity to warm-blooded animals, and can be used for combating arthropod pests, especially insects or acarids, which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the collembola, for example *Onychiurus armatus;* from the order of the Orthoptera, for example *Blatta orientalis Periplaneta americana, Leucophaea maderae, Blattella germanica, Acheta domesticus, Gryllotalpa* spp., *Locusta migratoria migratorioides, Melanoplus differentialis* and *Schistocerca gregaria;* from the order of the Dermaptera, for example *Forficula auricularia;* from the order of the Isoptera, for example *Reticulitermes* spp.;

from the order of the Anoplura, for example Phylloxera vastatrix, Pemphigus spp., *Pediculus humanus corporis, Haematopinus* spp. and *Linognathus* spp.;

from the order of the Mallophaga, for example *Tirchodectes* spp. and *Damalinea* spp.;

from the order of the Thysanoptera, for example *Hercinothrips femoralis* and *Thrips tabaci;* from the order of the Heteroptera, for example *Eurygaster* spp., *Dysdercus intermedius, Piesma quadrata, Cimex lectularius, Rhodnius prolixus* and *Triatoma* spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Laphygma exigua, Mamestra brassicae, Panolis flammea, Prodenia litura, Spodoptera* spp., *Trichoplusia ni, Carpocapsa pomonella, Pieris* spp., *Chilo* spp., *Pyrausta nubilalis,*

*Ephestia kuehniella, Galleria mellonella, Cacoecia podana, Capua reticulana, Choristoneura fumiferana, Clysia ambiguella, Homona magnanima* and *Tortrix viridana;* from the order of the *Coleoptera,* for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis* and *Costelytra zealandica;* from the order of the *Hymenoptera,* for example *Diprion* spp., *Hoplocampa* spp., *Lasius* spp., *Monomorium pharaonis* and *Vespa* spp.;

from the order of the *Diptera,* for example *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae* and *Tipula paludosa;* from the order of the *Siphonaptera,* for example *Xenopsylla cheopis* and *Ceratophyllus* spp.;

from the class of the *Arachnida,* for example *Scorpio maurus* and *Latrodectus mactans;* from the order of the *Acarina,* for example *Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., and *Tetranychus* spp..

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.001 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

In the veterinary field, the active compounds according to the invention may be used in a known manner, such as orally in the form of, for example, tablets, capsules, drenches and granules; dermally by means of, for example, dipping, spraying, pouring-on, spotting-on and powdering; and parenterally, for example by means of injections.

The active compounds according to the invention can also be used as a mixture with other known active compounds, such as phosphoric acid esters, carboxylic acid esters, including the natural and synthetic pyrethroids, carbamates or halogenoalkanes.

The active compounds according to the invention also exhibit a powerful fungitoxic and bacteriotoxic action. They do not damage crop plants in the concentrations required for combating fungi and bacteria. On these grounds they are also suitable for use as plant protection agents for combating fungi and bacteria. Fungitoxic agents are employed in plant protection for combating *Plasmodiophoromycetes, Comycetes, Chytridiomycetes, Zygomycetes, Ascomycetes, Basidiomycetes* and *Deuteromycetes*.

The active compounds according to the invention have a broad spectrum of action and can be used against parasitic fungi which infect above-ground parts of plants or attack the plants through the soil, as well as against seed-borne pathogens.

The invention also provides crop protected from damage by arthropods by being grown in areas in which immediately prior to and/or during the time of the growing a compound of the formula (I) was applied, alone or in admixture with a diluent or carrier.

It will be seen that the usual methods of providing a harvested crop may be improved by the present invention.

The compounds of the formula (I) can also be applied, in admixture with a diluent or carrier, to domesticated animals in order to free or protect them from ectoparasitical insects or acarids.

The preparation of some of the active compounds to be used according to the invention is illustrated in the following examples:

EXAMPLE 1

Process A

A mixture of 600 g of o-hydroxy-acetophenone, 1 liter of methanol and 630 g of 1-N-pyrrolidinylcyclopentene was warmed for 2 hours to the reflux temperature and was then concentrated. On fractional distillation the residue gave, in addition to first runnings, 770 g (86% of the theoretical yield) of 2,2-tetramethylenechroman-4-one; boiling point 100°–105° C./0.05 mm Hg (compound 1).

Process B 100 g of pyrrolidine were added to a mixture of 680 g of o-hydroxy-acetophenone, 1.5 liters of toluene and 550 g of cyclopentanone, and the batch was left to stand for 1 day at 25° C. and was then heated for 5 hours using a water separator. After cooling, the organic phase was extracted by shaking with 250 ml of 2 N NaOH, 700 ml of 2 N HCl and 500 ml of water and the toluene solution was dried over sodium sulphate, concentrated and distilled. 860 g (85% of the theoretical yield) of 2,2-tetramethylenechroman-4-one were obtained at a boiling point of 110°–120° C./0.1 mm Hg.

The 2,2-tetramethylenechroman-4-ones obtained in accodance with the two variants were identical; they showed the expected signals in the nuclear resonance spectrum and a strong band at 1680–1690 cm$^{-1}$ in the infra-red spectrum.

Using variant A, an o-hydroxy-arylcarbonyl compound of the general formula

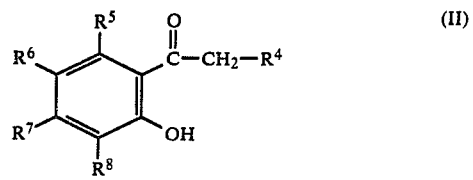

(II)

was reacted with an enamine of the general formula

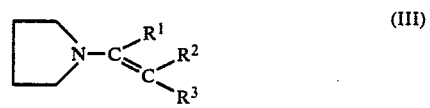

(III)

The table which follows indicates the particular substituents.

Using variant B, an o-hydroxy-arylcarbonyl compound of the general formula

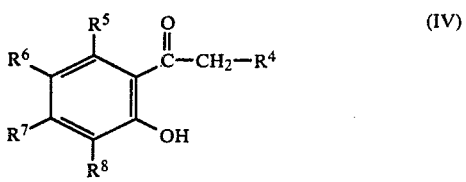

(IV)

was reacted with a carbonyl compound of the general formula

(V)

in the presence of pyrrolidine. The table which follows indicates the particular substituents. The table furthermore shows the molar amount of pyrrolidine, relative to the o-hydroxy-arylcarbonyl compound.

The chroman-4-ones listed in the table which follows were prepared in accordance with variant A or B.

Table 1

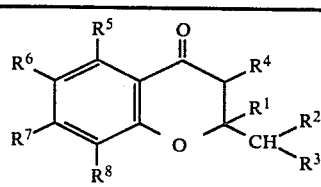

| Compound | $R^1$–$R^8$ | Process | Solvent | Time/temperature °C. | Amine (amount) | Yield | Boiling point °C./mm Hg (melting point °C.) |
|---|---|---|---|---|---|---|---|
| 2 | $R^1 + R^2 = -(CH_2)_4-$ | A | methanol | 24 hours/25° | | 89.3% | 130°/0.1 |

Table 1-continued

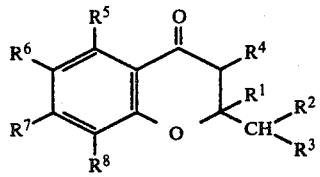

| Compound | $R^1$-$R^8$ | Process | Solvent | Time/temperature °C. | Amine (amount) | Yield | Boiling point °C./mm Hg (melting point °C.) |
|---|---|---|---|---|---|---|---|
| 3 | $R^1 + R^2 = -(CH_2)_4-$ | B | toluene | 2 hours/70°<br>6 hours/25°<br>2 hours/115° | pyrrolidine (1 mol) | 74% | 140°/0.2 |
| 4 | $R^1 + R^2 = -(CH_2)_6-$ | A | xylene | 3 hours/145° | | 20% | 170°/0.1 |
| 5 | $R^1 + R^2 = -(CH_2)_6-$ | B | toluene | 6 hours/25°<br>5 hours/115° | pyrrolidine (1 mol) | 67% | 170°/0.1 |
| 6 | $R^1 + R^2 = -(CH_2)_{10}-$ | B | toluene | 20 hours/25°<br>2 hours/115° | pyrrolidine (1 mol) | 53% | 220°/0.1<br>[93°-5°] |
| 7 | $R^1 + R^2 = -CH_2-CH_2-\underset{CH_3}{N}-CH_2$ | A | methanol | 2 hours/70° | | 96% | 135°/0.1 |
| 8 | $R^1 + R^2 = -CH_2-CH_2-\underset{COOC_2H_5}{CH}-CH_2$ | A | methanol | 24 hours/25° | | 55% | 190°/0.1 |
| 9 | $R^6 = Cl; R^1 + R^2 = -(CH_2)_4-$ | A | methanol | 24 hours/25° | | 72% | 155°/0.05 |
| 10 | $R^8 = Cl; R^1 + R^2 = -(CH_2)_4-$ | A | methanol | 24 hours/25° | | 69% | 160°/0.05 |
| 11 | $R^6 = CH_3O-; R^1 + R^2 = -(CH_2)_4-$ | A | methanol | 2 hours/70° | | 92% | 150°/0.05 |
| 12 | $R^8 = CH_3O; R^1 + R^2 = -(CH_2)_4-$ | A | methanol | 2 hours/70° | | 84% | 165°/0.05 |
| 13 | $R^2, R^3 = CH_3$ | A | methanol | 20 hours/25° | | 91% | 110°/0.1 |
| 14 | $R^2, R^3 = CH_3$ | B | toluene | 2 hours/115° | pyrrolidine (1 mol) | 93% | 110°/0.1 |
| 15 | $R^2 = CH_3-\text{C}_6H_4-$ | A | methanol | 2 hours/70° | | 15% | (118°-20°) |
| 16 | $R^2, R^3 = -CH_3; R^4 = CH_3; R^7 = Cl$ | A | toluene | 2½ hours/100° | | 70% | 130°/0.1 |
| 17 | $R^1 + R^2 = -(CH_2)_4-$<br>$R^7 = C_6H_5CH_2O-$ | A | methanol | 24 hours/25° | | 85% | (100-102°) |
| 18 | $R^2, R^3, R^6 = CH_3; R^4 = C_6H_5$ | A | without solvent | 3 hours/120° | | 71% | (75°-6°) |
| 19 | $R^1 = CH_3$ | B | toluene | 5 hours/25°<br>2 hours/80° | pyrrolidine (1 mol) | 50% | (88°-9°) |
| 20 | $R^2 = C_6H_5-CH_2$ | B | toluene | 20 hours/25°<br>1 hour/115° | pyrrolidine<br>1 mol:0.1 mol | 56%<br>34% | 185°/0.1<br>155°/0.1 |
| 21 | $R^1 = C_6H_5-CH_2$ | B | toluene | 2 hours/110° | pyrrolidine (1 mol) | 35% | 155°/0.1 |
| 22 | $R^2 = C_2H_5$ | B | toluene | 5 hours/25°<br>2 hours/reflux | pyrrolidine (1 mol) | 48% | 120°/0.05 |
| 23 | $R^1 = C_6H_5$ | B | toluene | 5 hours/105° | pyrrolidine (1 mol) | 14% | 160°/0.1 |
| 24 | $R^2 = $ n-pentyl | B | toluene | 2 hours/110° | pyrrolidine (1 mol) | 52% | 155°/0.1 |
| 25 | $R_1 = $ n-nonyl | B | toluene | 2 hours/110° | pyrrolidine (1 mol) | 63% | 175°/0.07 |
| 26 | $R^1 = -CH_2-CH_2-N(C_2H_5)_2$ | B | toluene | 4 hours/110° | pyrrolidine (0.3 mol) | 49% | 180°/0.2 |
| 27 | $R^1 + R^2 = (CH_2)_3$<br>$R^7 = C_2H_5OOC-CH_2O-$ | B | toluene | 20 hours/25°<br>2 hours/105° | pyrrolidine (0.2 mol) | 41% | 210°/0.2 |
| 28 | $R^1 = -(CH_2)_4 COOH$ | B | toluene | 24 hours/25°<br>2 hours/105° | pyrrolidine (1.2 mols) | 46% | 205°/0.1 |
| 29 | $R^1 = $ n-nonyl; $R^7 = OH$ | B | toluene | 24 hours/25°<br>2 hours/105° | pyrrolidine | 42% | 240°/0.1 |
| 30 | $R^1 = CH_2-COOC_2H_5$ | A | without solvent | 2 hours/180° | | 25% | 195°/0.1 |
| 31 | $R^1 = $ n-nonyl, $R^6 = OH$ | | | | | | |
| 32 | $R^1 = -(CH_2)_4-COOH, R^6 = CH_3O$ | | | | | | |
| 33 | $R^1 = -CH_2-CH_2-CH=C(CH_3)_2, R^6 = CH_3SO_2-O-$ | | | | | | |
| 34 | $R^1 + R^2 = -(CH_2)_3-, R^7 = OH$ | | | | | | |
| 35 | $R^1 + R^2 = -(CH_2)_3-, R^6, R^8 = Cl$ | | | | | | |
| 36 | $R^1 = -(CH_2)_3-N(C_2H_5)_2, R^6 = Cl$ | | | | | | |
| 37 | $R^1 = -CH_2-CH_2-CH=C(CH_3)_2, R^5 = OH, R^7 = $ 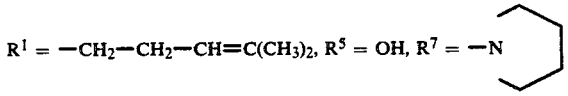 | | | | | | |
| 38 | $R^1 = -COOH$ | | | | | | |

Table 1-continued

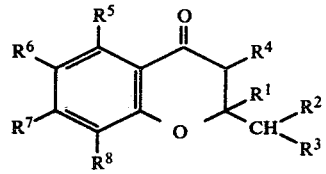

| Compound | $R^1$-$R^8$ | Process | Solvent | Time/temperature °C. | Amine (amount) | Yield | Boiling point °C./mm Hg (melting point °C.) |
|---|---|---|---|---|---|---|---|
| 39 | $R^1 = -CH_2-CH_2-COOH$, $R^5$, $R^7$, $R^8 = CH_3$, $R^6 = OH$ | | | | | | |

The arthropodicidal activity of the compounds of this invention is illustrated by the following examples wherein the compounds according to the present invention are each identified by the number (given in brackets) from example 1 hereinabove.

In the examples which follow, relating to the development-inhibiting action of the active compounds, the morphological changes, such as half-pupated animals, incompletely slipped larvae or caterpillars, defective wings, pupal cuticula in imagos and the like were rated as malformations throughout the entire stated development of the test animals. The sum of the morphological malformations, together with the animals destroyed during shedding or during metamorphosis, was determined in percent of the total number of the test animals.

EXAMPLE 2

Development-inhibiting action/ingestion test
Test animals: *Plutella maculipennis* (caterpillars in the 4th stage of development, 20 specimens) *Phaedon cochleariae* (larvae in the 4th stage of development, 20 specimens)
Feed plants: Cabbage plants (*Brassica oleracea*)
Solvent: 10 parts by weight of acetone
Emulsifier: 1 part by weight of alkylaryl polyglycol ether To produce a suitable preparation of active compound, 2 parts by weight of active compound were mixed with the stated amount of solvent, emulsifier and sufficient water to give a 1% strength mixture, which was diluted with water to the desired concentration.

The test animals were fed with leaves of the feed plants, which were provided with a uniform spray covering of the active compound mixture, so that the chosen concentration of active compound per unit area was obtained on the leaves, until the imago developed.

As a control, leaves coated only with solvent and emulsifier-water mixture of the chosen concentrations were used.

The results can be seen from the table which follows.

Table 2

| | Development-inhibiting action/ingestion test | | |
|---|---|---|---|
| | Plutella maculipennis | | Phaedon cochleariae |
| Active Compounds | % malformations at concentrations (by weight) of | | |
| | 0.01% | 0.001% | 0.01% |
| Control | 0% | 0% | 0% |
| Precocene I (known) | 60% | 0% | 0% |
| Precocene II (known) | 80% | 0% | 0% |
| (1) | 100% | 100% | 80% |

Table 2-continued

| | Development-inhibiting action/ingestion test | | |
|---|---|---|---|
| | Plutella maculipennis | | Phaedon cochleariae |
| Active Compounds | % malformations at concentrations (by weight) of | | |
| | 0.01% | 0.001% | 0.01% |
| (25) | 100% | 100% | 100% |
| (31) | 100% | 60% | 100% |
| (32) | 100% | 60% | — |
| (33) | 100% | 50% | — |
| (34) | 100% | 20% | 70% |
| (24) | — | — | 100% |
| (35) | — | — | 100% |
| (36) | — | — | 100% |

EXAMPLE 3

Development-inhibiting action/Laphygma egg test
Test animal: *Laphygma frugiperda* (eggs)
Feed: Corn (*Zea mays*)
Solvent: 10 parts by weight of acetone
Emulsifier: 1 part by weight of alkylaryl polyglycol ether To produce a suitable preparation of active compound, 2 parts by weight of active compound were mixed with the stated amount of solvent, emulsifier and sufficient water to produce a 1% strength mixture, which was diluted with water to the desired concentration.

Deposited eggs, at the rate of 30 eggs on a filter-paper, were moistened with 1 ml of active compound solution of the chosen concentration and were observed, in plastic boxes, until the young larvae slipped. The young larvae were fed with corn leaves which had been sprayed with the chosen concentration of active compound solution on the same day as the eggs. The development of the test animals was observed up to the larva of the 3rd stage.

As a control, deposited eggs were treated in the same manner with solvent and emulsifier-water mixture of the chosen concentration, and feeding was carried out with correspondingly treated corn leaves.

The results are shown in the table which follows:

Table 3

| | Development-inhibitin action/Laphygma egg test |
|---|---|
| Active compounds | % malformations at a concentration of 0.01% by weight |
| Control | 0% |
| Precocene I (known) | 0% |
| (31) | 100% |
| (37) | 100% |
| (33) | 100% |

Table 3-continued

| Development-inhibitin action/Laphygma egg test | |
|---|---|
| Active compounds | % malformations at a concentration of 0.01% by weight |
| (38) | 100% |
| (39) | 100% |

It will be appreciated that the instant specification and examples are set forth by way of illustration and not limitation, and that various modifications and changes may be made without departing from the spirit and scope of the present invention.

What is claimed is:

1. A method of combating arthropods which comprises applying to the arthropods, or to a habitat thereof, an arthropodicidally effective amount of a chroman-4-one of the formula

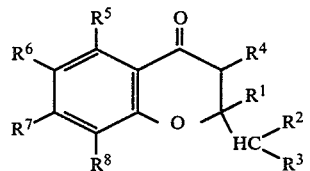

wherein $R^1$ to $R^4$, which need not be identical, each represent $C_1$–$C_{18}$ alkyl, $C_2$–$C_{18}$ alkenyl, $C_3$–$C_{18}$ cycloalkyl, $C_6$–$C_{14}$ aryl, aralkyl with 1 to 8 carbon atoms in the aliphatic part and 6 to 10 carbon atoms in the aromatic part, or alkoxycarbonyl with 1 to 18 carbon atoms in the alkyl part, any of these groups being optionally substituted by halogen, cyano, $C_1$–$C_6$-alkyl, $C_1$–$C_6$-alkoxy, ($C_1$–$C_6$-alkoxy)-carbonyl, ($C_1$–$C_6$-alkoxy)carbonyl($C_1$–$C_6$-alkyl), amino, $C_1$–$C_6$-alkylamino, di-($C_1$–$C_6$-alkyl)amino, aryl from the benzene series or a carboxylic acid group, or represent hydrogen, carboxyl or $C_1$–$C_{18}$ aminoalkyl, $R^2$ can alternatively represent amino or di-($C_1$–$C_{18}$-alkyl)amino which is optionally substituted by halogen, cyano, $C_1$–$C_6$-alkyl, $C_1$–$C_6$-alkoxy, ($C_1$–$C_6$-alkoxy)-carbonyl, ($C_1$–$C_6$-alkoxy)carbonyl($C_1$–$C_6$-alkyl), amino, $C_1$–$C_6$-alkylamino, di-($C_1$–$C_6$-alkyl)amino, aryl from the benzene series or a carboxylic acid group, or $R^1$ and $R^2$ can, conjointly with the adjoining carbon atoms, form a 3-membered to 12-membered saturated or unsaturated carbocyclic ring, which can be fused to a benzene ring, or form a 5-membered to 12-membered heterocyclic ring containing carbon atoms and one or more heteroatoms selected from nitrogen, oxygen and sulphur atoms, which heterocyclic ring can optionally contain one or two double bonds and can optionally be fused on a benzene ring, and $R^5$ to $R^8$, which need not be identical, each represent $C_1$–$C_{18}$ alkyl, $C_2$–$C_{18}$ alkenyl, $C_3$–$C_{18}$ cycloalkyl, $C_6$–$C_{14}$ aryl, aralkyl or aralkoxy with 1 to 8 carbon atoms in the aliphatic part and 6 to 10 carbon atoms in the aromatic part, $C_1$–$C_{18}$ alkoxy, $C_6$–$C_{14}$ aryloxy, alkoxycarbonyl with 1 to 18 carbon atoms in the alkyl part, $C_1$–$C_{18}$ alkylamino or di-($C_1$–$C_{18}$-alkyl)amino, any of these groups being optionally substituted by halogen, cyano, $C_1$–$C_6$-alkyl, $C_1$–$C_6$-alkoxy, ($C_1$–$C_6$-alkoxy)-carbonyl, ($C_1$–$C_6$-alkoxy)carbonyl($C_1$–$C_6$-alkyl), amino, $C_1$–$C_6$-alkylamino, di-($C_1$–$C_6$-alkyl)amino, aryl from the benzene series or a carboxylic acid group, or represent hydrogen, chlorine, hydroxyl, nitro, cyano, carboxyl, amino, aliphatic $C_1$–$C_{18}$ acylamino or aromatic $C_6$–$C_{14}$ acylamino.

2. The method according to claim 1, wherein the compound is applied to a domesticated animal.

* * * * *